United States Patent
McClements et al.

(10) Patent No.: US 10,357,049 B2
(45) Date of Patent: Jul. 23, 2019

(54) SPONTANEOUS ANTIMICROBIAL ESSENTIAL OIL NANOEMULSIONS AND THEIR USE AS A FOOD AND SURFACE DISINFECTANT/SANITIZER

(71) Applicant: THE UNIVERSITY OF MASSACHUSETTS, Boston, MA (US)

(72) Inventors: David J. McClements, Northampton, MA (US); Lynne McLandsborough, Sunderland, MA (US); Kyle Landry, Sunderland, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 196 days.

(21) Appl. No.: 15/216,895

(22) Filed: Jul. 22, 2016

(65) Prior Publication Data
US 2017/0020171 A1    Jan. 26, 2017

Related U.S. Application Data

(60) Provisional application No. 62/196,666, filed on Jul. 24, 2015.

(51) Int. Cl.
| | | |
|---|---|---|
| *A23L 3/3472* | (2006.01) | |
| *A01N 31/08* | (2006.01) | |
| *A01N 25/04* | (2006.01) | |
| *A23L 3/3508* | (2006.01) | |

(52) U.S. Cl.
CPC ............ *A23L 3/3472* (2013.01); *A01N 25/04* (2013.01); *A01N 31/08* (2013.01); *A23L 3/3508* (2013.01); *Y02A 40/943* (2018.01); *Y02A 40/944* (2018.01)

(58) Field of Classification Search
CPC ........ A23L 3/3472; A23L 3/3508; A23L 3/00; A01N 31/08; A01N 25/04; A23N 25/00; A23N 25/02; A23N 25/04; Y02A 40/90; Y02A 40/943; Y02A 40/944
USPC ....................................................... 426/310
See application file for complete search history.

(56) References Cited

U.S. PATENT DOCUMENTS

| 2011/0086117 A1* | 4/2011 | Khunkitti ............... A01N 65/00 424/750 |
| 2012/0145086 A1 | 6/2012 | Ochomogo et al. |
| 2015/0051298 A1 | 2/2015 | McClements et al. |

FOREIGN PATENT DOCUMENTS

WO    WO-2009118120 A1 *    10/2009    ........... H01H 9/0072

OTHER PUBLICATIONS

Asker et al "formation and stabilization of antimicrobial Delivery systems . . . polysaccharides", J. of Agric. Food Chem 2011, vol. 59 pp. 1041-1049 (Year: 2011).*
Bouchemal et al.; "Nano-emulsion Formulation Using Spontaneous Emulsification: Solvent, Oil and Suractant Optimisation"; International Journal of Pharmaceutics: 280; pp. 241-251; (2004).
Chang et al.; Fabrication, Stability and Efficacy of Dual-Component Antimicrobial Nanoemulsions: Essential Oil (Thyme Oil) and Catonic Surfactant (Lauric Arginate); Food Chemistry; 172; pp. 298-304; (2015).
Gulotta et al.; "Nanoemulsion-Based Delivery Systems for Polyunsaturated (w-3) Oils: Formation Using a Spontaneous Emulsification Method"; J. Agric. Food Chem; 62; pp. 1720-1725; (2014).
Mayer et al.; "Vitamin E-enriched Nanoemulsions Formed by Emulsion Phase Inversion: Factors Influencing Droplet Size and Stability"; Journal of Colloid and Interface Science; 402; pp. 122-130; (2013).
Saberi et al.; "Effect of Glycerol on Formation, Stability, and Properties of Vitamin-E Enriched Nanoemulsions Produced Using Spontaneous Emulsification"; Journal of Colloid and Interface Science; 411; pp. 105-113; (2013).
Saberi et al.; "Fabrication of Vitamin E-enriched Nanoemulsions: Factors Affecting Particle Size Using Spontaneous Emulsification"; Journal of Colloid and Interface Science; 391; pp. 95-102; (2013).

* cited by examiner

*Primary Examiner* — Jyoti Chawla
(74) *Attorney, Agent, or Firm* — Cantor Colburn LLP (57) ABSTRACT

The use of low energy spontaneous emulsification method to fabricate acidified antimicrobial nanoemulsions suitable for utilization as a food disinfectant/sanitizer is described. The method of these teachings includes pouring an organic phase (containing oil and surfactant and oil-soluble components) into an aqueous phase (containing water and water-soluble components), which leads to the spontaneous formation of fine droplets due to rapid diffusion of the surfactant from the oil phase into the aqueous phase.

8 Claims, 4 Drawing Sheets

SPONTANEOUS ANTIMICROBIAL ESSENTIAL OIL NANOEMULSIONS AND THEIR USE AS A FOOD AND SURFACE DISINFECTANT/SANITIZER

CROSS REFERENCE TO RELATED APPLICATIONS

This application claims priority to U.S. Provisional Patent Application No. 62/196,666, filed on Jul. 24, 2015, entitled SPONTANEOUS ANTIMICROBIAL ESSENTIAL OIL NANOEMULSIONS AND THEIR USE AS A FOOD AND SURFACE DISINFECTANT/SANITIZER, which is incorporated by reference herein in its entirety for all purposes.

BACKGROUND

These teachings relate generally to the fabrication and use of antimicrobial nanoemulsions for the treatment of foods and surfaces.

Emulsions containing very fine droplets (radius≈<100 nm) are referred to as nanoemulsions. Nanoemulsions can be formed from both high-energy and low-energy methods. High energy methods require specialized mechanical devices that are capable of generating intense mechanical forces that can intermingle and disrupt the oil and water phases, such as sonicators, high pressure valve homogenizers, or microfluidizers. Low-energy methods rely on the spontaneous formation of fine oil droplets due to physicochemical processes that occur when certain combinations of surfactant, oil, and water are combined under appropriate conditions The use of low-energy methods is highly attractive for preparing nanoemulsions for many applications because of its low cost and simplicity. A number of low-energy methods are available for producing nanoemulsions, e.g., spontaneous emulsification, emulsion inversion point, phase inversion temperature, and phase inversion composition methods. The spontaneous emulsification method is one of the suitable for commercial implementation since it simply involves titrating a mixture of oil and water-soluble surfactant into water. This method has recently been reported to be suitable for application in the food industry for fabricating effective antimicrobial nanoemulsions from essential oils.

Essential oils are natural compounds that are isolated from various plant sources such as thyme, oregano, and basil that demonstrate antimicrobial activity. One essential oil that has been shown to have promising antimicrobial properties against a variety of foodborne pathogens is carvacrol. Essential oils, alone, have minimal solubility in water.

The use of essential oils, such as carvacrol, as antimicrobials is appealing because these compounds are a "natural" alternative to traditional treatment methods. The effectiveness of carvacrol against various foodborne pathogens has been reported in numerous studies. The antimicrobial efficacy of carvacrol has been attributed to its ability to permeabilize and depolarize the cytoplasmic membrane. This phenomenon is a result of the hydrophilic hydroxyl group on the phenolic ring, which allows carvacrol to dissolve into and disrupt cytoplasmic membrane function. However, even with this hydrophilic moiety, carvacrol is still predominantly hydrophobic and therefore has low water-solubility.

Both acetic and levulinic acid are proven antimicrobial compounds that have wide acceptability in the food safety community. Organic acids have a direct impact on the intracellular pH of pathogens. Protonated organic acids can pass through the outer membrane of bacteria and once in the cytoplasm, dissociate, releasing protons and anions inside the cell. This sudden influx of charged compounds disrupts a cells homeostasis by acidifying the cytoplasm. If acid levels are high enough, functional enzyme denaturation will occur ultimately leading to cell death.

In view of the number of the possible applications for the treatment of fruits and surfaces, there is a need for a method for preparing stable nanoemulsions with desired antimicrobial performance.

BRIEF SUMMARY

The present teachings describe the use of low energy spontaneous emulsification method to fabricate acidified multi-antimicrobial nanoemulsions suitable for utilization as a food disinfectant/sanitizer. In one or more embodiments, the method of these teachings includes pouring an organic phase (containing oil and surfactant and oil-soluble components) into an aqueous phase (containing water and water-soluble components), which leads to the spontaneous formation of fine droplets due to rapid diffusion of the surfactant from the oil phase into the aqueous phase. In one or more embodiments, the acidified essential oil antimicrobial nanoemulsions of these teachings are used for the treatment of foods and surfaces. This method allows stable essential oil NEs to be fabricated at room temperature using simple stirring, rather than expensive homogenization equipment. This approach may therefore be particularly suitable for utilization in the food and other industries. The antimicrobial system of these teachings can be applied to all foodborne pathogens.

For a better understanding of the present teachings, together with other and further needs thereof, reference is made to the accompanying drawings and detailed description and its scope will be pointed out in the appended claims.

DETAILED DESCRIPTION

The following detailed description presents the currently contemplated modes of carrying out the invention. The description is not to be taken in a limiting sense, but is made merely for the purpose of illustrating the general principles of the invention, since the scope of the invention is best defined by the claims.

The mass fraction is the ratio of one substance with mass to the mass of the total mixture. The mass fraction can be expressed as a percentage.

The present teachings describe the use of low energy spontaneous emulsification method to fabricate acidified multi-antimicrobial nanoemulsions suitable for utilization as a food disinfectant/sanitizer. In one or more embodiments, the method of these teachings includes pouring an organic phase (containing oil and surfactant and oil-soluble components) into an aqueous phase (containing water and water-soluble components), which leads to the spontaneous formation of fine droplets due to rapid diffusion of the surfactant from the oil phase into the aqueous phase. In one or more embodiments, the acidified essential oil antimicrobial nanoemulsions of these teachings are used for the treatment of foods and surfaces. This method allows stable essential oil NEs to be fabricated at room temperature using simple stirring, rather than expensive homogenization equipment. This approach may therefore be particularly suitable for utilization in the food and other industries industry.

While the exemplary embodiments presented hereinbelow use one of two essential oils and one of two organic acids, it should be noted that other essential oils and organic acids are within the scope of these teachings.

Essential oils include, but are not limited to, rosemary, oregano, lemongrass, sage, clove, thyme, turmeric, and tea bush oils and others and all purified essential oil components (such as, but not limited, to, α terpineol, carvacrol, citral, eugenol, geraniol, thymol and others). Organic acids include, but are not limited to, Acetic acid (used in one exemplary embodiment), Levulinic acid (used in one exemplary embodiment), Citric acid (including citrate), Lactic acid, Malic acid and Gluconic acid.

In an aspect, the aqueous phase comprises an organic acid having a pH of between 2 and 4.5.

Exemplary embodiments are presented hereinbelow. It should be noted that these teachings are not limited only to the exemplary embodiments. In the exemplary embodiments presented hereinbelow, two different essential oils and two different organic acids are used.

The spontaneous emulsification of carvacrol, originally put forth by Chang et al., is simple to produce and requires minimal equipment and training (Chang, Y.; McLandsborough, L.; McClements, D. J., Physicochemical properties and antimicrobial efficacy of carvacrol nanoemulsions formed by spontaneous emulsification. *Journal of agricultural and food chemistry* 2013, 61, 8906-13, which is incorporated by reference herein in its entirety and for all purposes.). The nanoemulsion has also been shown to be effective against foodborne pathogens in both in vitro and in vivo sprout setting. In a broth-based system, the minimal inhibitory concentration for the spontaneous carvacrol nanoemulsion was found to be 500 ppm, with complete inactivation at concentrations greater than or equal to 4000 ppm. When applied to a sprout based system, a 60 min treatment in 4,000 or 8,000 ppm carvacrol nanoemulsion resulted in complete inactivation of both *Salmonella Enteritidis* and *Escherichia coli* O157:H7 on both mung bean and alfalfa seeds. Previously reports have demonstrated that the combination of the 50 mM levulinic acid and the surfactant sodium dodecyl sulfate can inactivate pathogens on alfalfa seeds. For the spontaneous carvacrol nanoemulsion disclosed herein below, Tween 80® is the main surfactant used in the system. To see if organic acids may be beneficial, acetic or levulinic acid was added to the nanoemulsion formulation and its efficacy tested on artificially contaminated surfaces and produce.

The spontaneous emulsification process utilized herein, allows for the dispersion of essential oils into aqueous phases in the form of small oil droplets. In a water-dispersible form, carvacrol is able to act on any pathogens also present in the surrounding aqueous phase or at surfaces.

Antimicrobial spontaneous nanoemulsions, as reported herein below and in Chang et al., have a weight percentage of essential oil between 2.5% wt and 4% wt and a weight percentage of carrier oil between 6% wt and 7.5% wt (while keeping the oil blend at 10% wt) and a weight percentage of surfactant varying from 5% wt to 20% wt, preferably from 10% wt to 20% wt. The weight percentage of the aqueous phase completes the 100%.

Bacterial Strains and Culture Conditions

The bacterial cultures used in the exemplary embodiments were *Salmonella enterica* subspecies enterica serovar *Enteritidis* strains 709 (ATCC BAA-709), 711 (ATCC BAA-711), and 1045 (ATCC BAA-1045). Stock cultures of each organism were stored at −80° C. in tryptic soy broth (TSB; BD Diagnostic Systems, Cat #DF0064-07-6) containing 25% (v/v) glycerol. Monthly, frozen stock cultures were transferred to working cultures by plating on tryptic soy agar (TSA, BD Diagnostic Systems, Cat #DF0370-075) slants/plates and incubating at 37° C. for 24 hrs. The absorbance at 600 nm was used to determine cells numbers, with an absorbance of 0.5 equal to $1.5 \times 10^8$ CFU for all *Salmonella Enteritidis* strains as determined by plate counts.

Periodically, working cultures were streaked on differential media to ensure purity. For *S. Enteritidis*, cultures were spread on xylose, lysine, deoxycholate (XLD) agar (Remel Cat #R459902). Cultures were incubated overnight in TSB at 37° C. on a rotary shaker set at 150 RPM. All cultures were diluted with TSB to the desired cell numbers.

Fabrication of Acidified Carvacrol Nanoemulsions by Spontaneous Emulsification

The preparation of the antimicrobial nanoemulsion was based on a method cited herein below, but with a few modifications. Carvacrol (4 g) (Sigma-Aldrich, Cat #W224502-100G-K) was added to 6 g of medium chain triglyceride (MCT) oil (Miglyol 812, Witten, Germany) and thoroughly mixed with a magnetic stir bar for 5 min at 125 rpm, Once mixed, Tween 80® (10 g) (Sigma-Aldrich, Cat #P1754-500 ml) was added to the oil mixture and mixed with a magnetic stir bar for another 5 min at 125 rpm. The oil/Tween 80 mixture (20 g) was titrated, at a rate of 2 mL/min, into 80 g of either 50 mM levulinic (pH 2.8; Sigma-Aldrich, Cat #W262706) or acetic acid buffer (pH 2.5; Macron chemical, Cat #V196-05) containing a magnetic stirring bar set to 600 rpm and allowed to mix for an additional 15 min. The emulsion was filter sterilized through a sterile 0.45 μm syringe filter (Fisher Scientific Cat #09-719-005) and stored in sterile 50 mL conical tubes at 2-5° C. for up to 3 weeks. Droplet size was measured using dynamic light scattering (Zetasizer Nano ZS, Malvern Instruments, UK).

(1) Formation and Stability of Acidified Essential Oil Spontaneous Nanoemulsion

Figure 1:
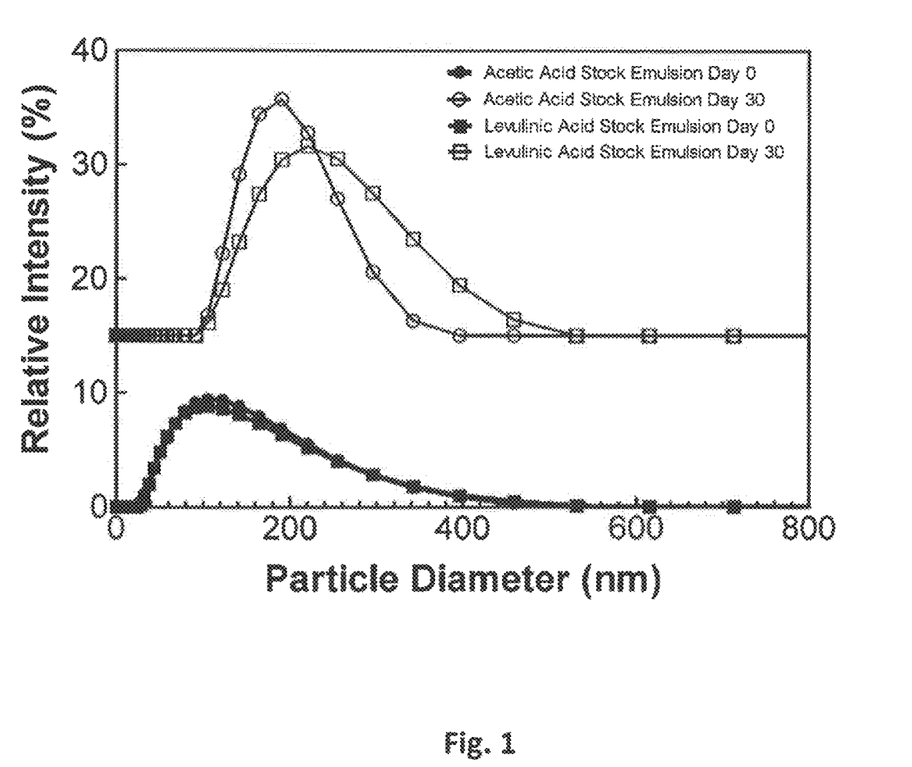
FIG. 1 shows comparison of the mean diameter (Z-average) of freshly prepared and stored (30 days) acidified carvacrol nanoemulsion; to distinguish between the samples, 15 units were added to the relative intensity of the 30 day sample.
Figure 2:
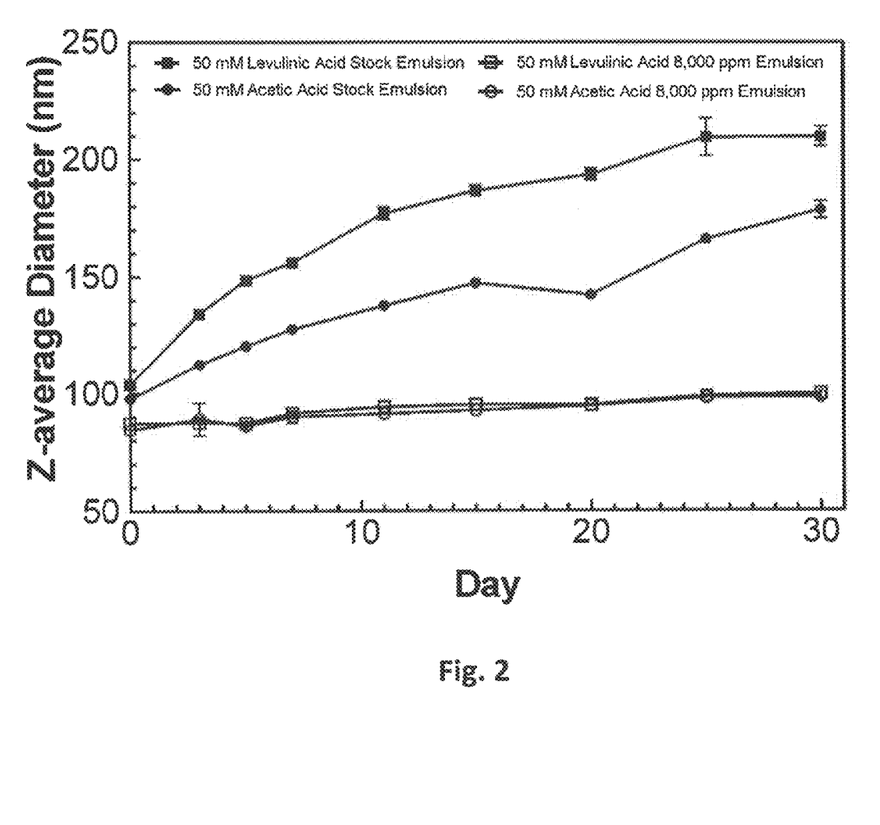
FIG. 2 show a Comparison of the increase in mean droplet diameter (Z average) of undiluted and 5-fold diluted acidified spontaneous carvacrol nanoemulsion when stored for 30 days; all plotted means and standard deviations are from triplicate studies.
Figure 3:
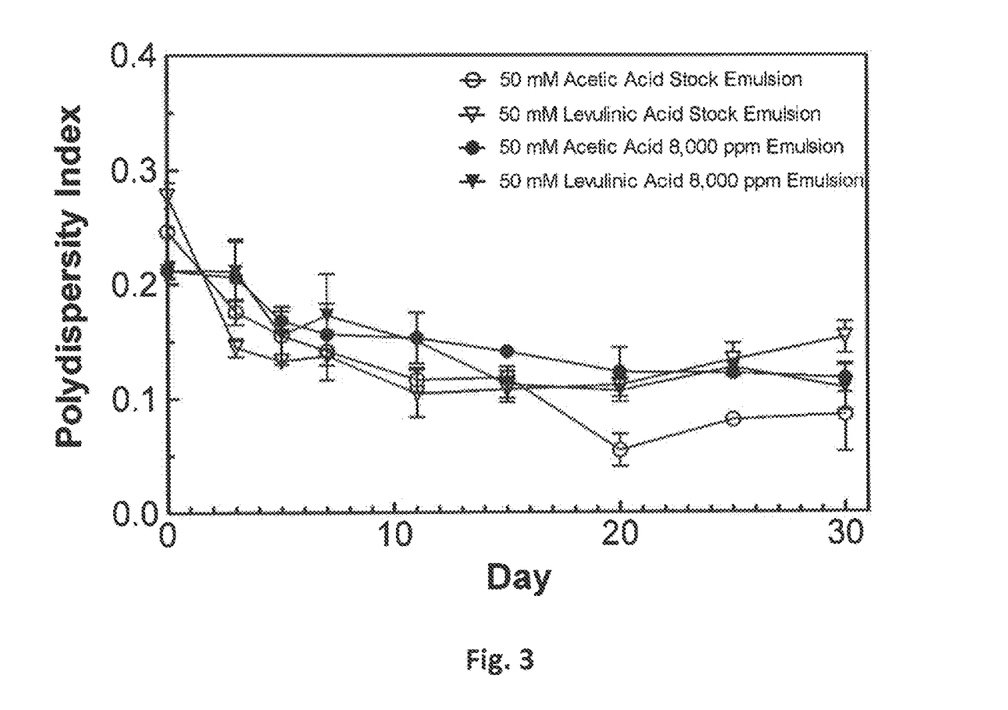
FIG. 3 depicts a comparison of the change in polydispersity index of undiluted and 5-fold diluted acidified spontaneous carvacrol nanoemulsion when stored for 30 days; all plotted means and standard deviations are from triplicate studies.

Nanoemulsions were prepared using the spontaneous emulsification method described in U.S. patent application Ser. No. 14/458,517, published as U.S. Publication No, US-2015-0051298-A1, which is incorporated by reference herein in its entirety and for all purposes. The freshly prepared nanoemulsions with a concentration of 8,000 ppm carvacrol had mean droplet diameters (Z-average) around 90 nm for both acetic and levulinic acid compared to a mean particle diameter of approximately 100 nm at a concentration of 40,000 ppm carvacrol in acetic acid (FIG. 1 and FIG. 2). After 30 days, the particle size had increased to approximately 100 nm for emulsions prepped at 8,000 ppm and 180 nm for emulsions prepped at 40,000 ppm. (FIG. 1 and FIG. 2). Additionally, the polydispersity index decreased over time for all emulsions tested (FIG. 3). These results indicate that while the droplet size is growing, it is also becoming more uniform with time. This is likely due to Ostwald Ripening, as the carvacrol may be moving from the oil droplet into the aqueous phase. However, when efficacy was tested after 30 days of storage the emulsion system was still effective. Previous results showed that growth in droplet size during storage could be inhibited by diluting the nanoemulsion 5-fold with sterile sodium citrate buffer prior to storage. It was observed that stability was greatly enhanced with dilution.

FIG. 1 shows Comparison of the mean diameter (Z-average) of freshly prepared and stored (30 days) acidified carvacrol nanoemulsion; to distinguish between the samples. 15 units were added to the relative intensity of the 30 day sample.

FIG. 2 shows a comparison of the increase in mean droplet diameter (Z average) of undiluted and 5-fold diluted acidified spontaneous carvacrol nanoemulsion when stored for 30 days. All plotted means and standard deviations are from triplicate studies.

FIG. 3 shows a comparison of the change in polydispersity index of undiluted and 5-fold diluted acidified spontaneous carvacrol nanoemulsion when stored for 30 days. All plotted means and standard deviations are from triplicate studies.

Effectiveness of Acidified Carvacrol Nanoemulsion on Contaminated Sprouting Seeds All beans/seeds used in the exemplary embodiment detailed below were generously provided by Jonathan's Organics (Rochester, Mass.). Beans/seeds were inoculated and sprouted using a modified version of the methods presented by Ye et al. and Fransisca et al. (Ye, J.; Kostrzynska, M.; Dunfield, K.; Warriner, K., Control of *Salmonella* on sprouting mung bean and alfalfa seeds by using a biocontrol preparation based on antagonistic bacteria and lytic bacteriophages *Journal of food protection* 2010, 73, 9-17; Fransisca, L.; Zhou, B.; Park, H.; Feng, H., The effect of calcinated calcium and chlorine treatments on *Escherichia coli* O157:H7 87-23 population reduction in radish sprouts, *J Food Sci* 2011, 76, M404-12, both of which are incorporated by reference herein in their entirety and for all purposes). Batches (20 g) of beans/seeds were soaked in 50 mL of diluted *S. Enteritidis* cocktail for 20 min resulting in final inoculums of 8, 5, 4, 3, or 2 log CFU/g. The inoculated beans/seeds were then transferred to a sterile glass petri dish containing sterile filter paper (Fisher Scientific Cat #09-803-6D) within a biological safety cabinet, and allowed to dry overnight at ambient temperature. The inoculated bean/seed batches were placed in 250-mL beakers and treated by soaking in 50 mL of acidified nanoemulsion (4,000 or 8,000 ppm) with agitation (125 RPM) for 30 or 60 mins. For the control, contaminated batches were soaked in either 50 mM levulinic (pH 2.8; Sigma-Aldrich, Cat #W262706) or acetic acid (pH 2.5; Macron chemical, Cat #V196-05) buffer. After treatment, the batches were rinsed once with 50 mL of sterile deionized water and transferred to a sterile 250 mL beaker containing 50 mL of TSB. The beaker was placed on a rotary shaker set to 50 rpm for 15 min. After agitation, a dilution series was created and plated on the appropriate media and incubated at 37° C. for 24 hrs. For samples that would theoretically result in negative plate counts or that had low initial inoculation levels (2 and 3 log CFU/g), a three tube most probable number (MPN) assay was used in conjunction with spread plating according to the FDA's Bacteriological Analytical Manual (BAM). Samples were appropriately diluted in Lactose Broth (BD BBL Cat #DF0004-17.7) *Salmonella* enrichment and incubated overnight. Dilution sets were checked for turbidity. Any positive tubes were streaked on XLD media (Remel Cat #R459902) for confirmation. Both treated inoculated and uninoculated samples were then sprouted.

Treated inoculated and uninoculated mung beans (20 g) were transferred to a sterile 1000 mL bottle and soaked in 150 mL of distilled water at 20° C. for 24 hrs. The water was removed, and sprouting continued for 4 days at 20° C., with daily water by a 5-min soak in 150 mL of distilled water. After four days, two 25 g batches of sprouts were taken for microbiological testing. The samples were suspended in 225 mL of 0.1% peptone water and stomached for 1 min. A dilution series was created and plated on the appropriate media as previously described.

Batches (10 g) of inoculated and uninoculated broccoli seeds were transferred to a sterile 250 mL beaker and soaked in 150 mL of distilled water at 20° C. for 24 hours. The water was removed, and the seeds transferred to 3 pieces of sterile filter paper (Fisher Scientific Cat #09-803-6D) on top of a sterile plastic test tube rack in a sterile stainless steel container with a lid. The seeds were sprouted in the dark at 20° C. for 3 days. The seeds were watered with 15 mL of distilled water every 8 hrs with a plastic spray bottle (Fisher Scientific Cat #03-438-12A). After sprouting, two 25 g batches of sprouts were suspended in 225 mL of 0.1% peptone water and stomached for 1 min. A dilution series was created and plated on the appropriate media as previously described.

(1) Effectiveness of an Acidified Carvacrol Nanoemulsion Against *Salmonella* spp. Contaminated Mung Bean and Broccoli Seeds.

The effectiveness of either a levulinic or acetic acid acidified carvacrol nanoemulsion can be seen in Tables 1-4. Using an MPN assay, final *Salmonella Enteritidis* levels of ≤3 CFU/g were found on mung bean seeds that had an initial inoculum of 4 log CFU/g when treated with 4000 or 8000 ppm of carvacrol acidified with either organic acid (Table 1 and 2). Treatment of contaminated broccoli seeds with 4000 or 8000 ppm for both treatment times wither either organic acid yielded similar results for seeds with an initial inoculum of 2 log CFU/g (Table 3 and 4). Treatments that resulted in MPN numbers of ≤3 CFU/g were germinated and tested again for the presence of the pathogens using both plate counts and MPN. Following germination and microbiological testing, no *S. Enteritidis* was detected. These findings suggest that treatments were able to inactive *S. Enteritidis*. Total sprout yield was not compromised by any treatment (Table 5 and 6),

TABLE 1

Effect of carvacrol emulsion acidified with levulinic acid on contaminated mung beans [1,2]

| Treatment | Treatment Time (min) | Initial Inoculum (log CFU/g) | Cell Numbers after Treatment (log CFU/g) | Total Log Reduction | Pathogen Detected after Sprouting |
|---|---|---|---|---|---|
| Control | 30 | 8.6 ± 0.72 | 7.7 ± 0.65 | 0.75 ± 0.43 | + |
|  |  | 5.8 ± 0.68 | 4.9 ± 0.20 | 0.68 ± 0.83 | + |
|  |  | 4.3 ± 0.34 | 3.9 ± 0.53 | 0.63 ± 0.50 | + |
|  | 60 | 8.8 ± 0.04 | 7.9 ± 0.50 | 1.02 ± 0.53 | + |
|  |  | 5.8 ± 0.28 | 5.3 ± 0.61 | 0.71 ± 0.62 | + |
|  |  | 4.7 ± 0.28 | 4.1 ± 0.27 | 0.64 ± 0.42 | + |
| 8000 ppm | 30 | 8.5 ± 0.53 | 3.5 ± 0.45 | 5.01 ± 0.15 | + |
|  |  | 5.3 ± 0.44 | 1.5 ± 0.10 | 3.9 ± 0.54 | + |
|  |  | 4.6 ± 0.66 | ND | 4.6 ± 0.66 | − |
|  | 60 | 8.4 ± 0.50 | 3.8 ± 0.35 | 4.5 ± 0.48 | + |
|  |  | 5.5 ± 0.57 | 1.3 ± 0.20 | 4.0 ± 0.60 | + |
|  |  | 4.4 ± 0.60 | ND | 4.4 ± 0.60 | − |
| 4000 ppm | 30 | 8.4 ± 0.11 | 3.6 ± 0.76 | 5.1 ± 0.86 | + |
|  |  | 5.3 ± 0.73 | 1.4 ± 0.27 | 3.7 ± 0.47 | + |
|  |  | 4.6 ± 0.73 | ND | 4.6 ± 0.73 | − |
|  | 60 | 8.6 ± 0.34 | 3.6 ± 0.32 | 5.0 ± 0.22 | + |
|  |  | 5.6 ± 0.84 | 1.2 ± 0.21 | 4.0 ± 1.02 | + |
|  |  | 4.5 ± 0.75 | ND | 4.5 ± 0.75 | − |

[1] All means and standard deviations are from triplicate studies. A "ND" indicates that no pathogens were detected using a three-tube MIN assay. Following treatment, seeds were germinated and tested for the presence of pathogens. A "+" indicates that pathogens were detected after germination. A "−" indicates that no pathogens were detected after germination.

[2] Total reduction averages within each treatment grouping were compared using Tukey's Test with a 95% confidence interval. Groupings of statistical significance are indicated by superscripted letters.

TABLE 2

Effect of carvacrol emulsion acidified with acetic acid on contaminated mung beans [1,2]

| Treatment | Treatment Time (min) | Initial Inoculum (log CFU/g) | Cell Numbers after Treatment (log CFU/g) | Total Log Reduction | Pathogen Detected after Sprouting |
|---|---|---|---|---|---|
| Control | 30 | 8.2 ± 0.08 | 7.4 ± 0.51 | 0.87 ± 0.53 | + |
|  |  | 5.2 ± 0.40 | 4.8 ± 0.88 | 0.78 ± 0.84 | + |
|  |  | 4.7 ± 0.45 | 3.8 ± 0.16 | 0.80 ± 0.64 | + |
|  | 60 | 8.7 ± 0.04 | 7.9 ± 0.50 | 1.03 ± 0.53 | + |
|  |  | 5.8 ± 0.68 | 4.9 ± 0.20 | 0.69 ± 0.83 | + |
|  |  | 4.3 ± 0.28 | 4.0 ± 0.60 | 0.53 ± 0.82 | + |
| 8000 ppm | 30 | 8.3 ± 0.31 | 3.6 ± 0.65 | 4.9 ± 0.52 | + |
|  |  | 5.3 ± 0.46 | 1.4 ± 0.09 | 3.7 ± 0.48 | + |
|  |  | 4.5 ± 0.74 | ND | 4.5 ± 0.74 | − |
|  | 60 | 8.9 ± 0.84 | 3.9 ± 0.19 | 4.6 ± 0.91 | + |
|  |  | 5.1 ± 0.58 | 1.1 ± 0.05 | 3.8 ± 0.62 | + |
|  |  | 4.0 ± 0.22 | ND | 4.0 ± 0.22 | − |
| 4000 ppm | 30 | 8.4 ± 0.30 | 3.3 ± 0.16 | 5.0 ± 0.30 | + |
|  |  | 5.0 ± 0.47 | 1.4 ± 0.01 | 3.5 ± 0.46 | + |
|  |  | 4.2 ± 0.47 | ND | 4.2 ± 0.47 | − |
|  | 60 | 8.2 ± 0.40 | 3.4 ± 0.51 | 4.9 ± 0.89 | + |
|  |  | 5.1 ± 0.59 | 1.3 ± 0.20 | 3.6 ± 0.62 | + |
|  |  | 4.3 ± 0.46 | ND | 4.3 ± 0.46 | − |

[1] All means and standard deviations are from triplicate studies. A "ND" indicates that no pathogens were detected using three-tube MPN assay. Following treatment; seeds were germinated and tested for the presence of pathogens. A "+" indicates that pathogens were detected after germination. A "−" indicates that no pathogens were detected after germination.

[2] Total reduction averages within each treatment grouping were compared using Tukey's Test with a 95% confidence interval. Groupings of statistical significance are indicated by superscripted letters.

TABLE 3

Effect of carvacrol emulsion acidified with levulinic acid on contaminated broccoli seeds [1,2]

| Treatment | Treatment Time (min) | Initial Inoculum (log CFU/g) | Cell Numbers after Treatment (log CFU/g) | Total Log Reduction | Pathogen Detected after Sprouting |
|---|---|---|---|---|---|
| Control | 30 | 8.4 ± 0.43 | 7.5 ± 0.35 | 0.83 ± 0.58 | + |
| | | 5.7 ± 0.86 | 4.7 ± 0.38 | 0.47 ± 0.55 | + |
| | | 3.3 ± 0.52 | 3.0 ± 0.44 | 0.30 ± 0.91 | + |
| | | 2.5 ± 0.13 | 2.3 ± 0.31 | 0.29 ± 0.37 | + |
| | 60 | 8.5 ± 0.42 | 7.6 ± 0.10 | 0.74 ± 0.46 | + |
| | | 5.6 ± 0.24 | 5.4 ± 0.67 | 0.38 ± 0.85 | + |
| | | 3.6 ± 0.60 | 3.3 ± 0.59 | 0.27 ± 0.22 | + |
| | | 2.5 ± 0.12 | 2.3 ± 0.12 | 0.20 ± 0.09 | + |
| 8000 ppm | 30 | 8.5 ± 0.23 | 5.1 ± 0.20 | 3.4 ± 0.41 | + |
| | | 5.6 ± 0.33 | 3.8 ± 0.38 | 1.8 ± 0.65 | + |
| | | 3.8 ± 0.14 | 2.8 ± 0.40 | 1.1 ± 0.52 | + |
| | | 2.4 ± 0.09 | ND | 2.4 ± 0.09 | − |
| | 60 | 8.3 ± 0.48 | 5.1 ± 0.11 | 2.9 ± 0.37 | + |
| | | 5.6 ± 0.44 | 2.8 ± 0.82 | 2.9 ± 0.88 | + |
| | | 3.9 ± 0.54 | 2.6 ± 0.16 | 1.2 ± 0.62 | + |
| | | 2.1 ± 0.30 | ND | 2.1 ± 0.30 | − |
| 4000 ppm | 30 | 8.0 ± 0.12 | 5.4 ± 0.17 | 2.6 ± 0.08 | + |
| | | 5.9 ± 0.28 | 3.9 ± 0.43 | 2.09 ± 0.16 | + |
| | | 3.8 ± 0.20 | 2.8 ± 0.11 | 0.97 ± 0.31 | + |
| | | 2.6 ± 0.09 | ND | 2.6 ± 0.09 | − |
| | 60 | 8.1 ± 0.26 | 5.3 ± 0.23 | 2.8 ± 0.49 | + |
| | | 5.7 ± 0.51 | 3.9 ± 0.17 | 1.7 ± 0.46 | + |
| | | 3.8 ± 0.38 | 2.6 ± 0.15 | 1.1 ± 0.40 | + |
| | | 2.6 ± 0.15 | ND | 2.6 ± 0.15 | − |

[1] All means and standard deviations are from triplicate studies. A "ND" indicates that no pathogens were detected using a three-tube MPN assay. Following treatment, seeds were germinated and tested for the pretence of pathogens. A "+" indicates that pathogens were detected after germination. A "−" indicates that no pathogens were detected after germination.
[2] Total reduction averages within each treatment grouping were compared using Tukey's Test with a 95% confidence interval. Groupings of statistical significance are indicated by superscripted letters.

TABLE 4

Effect of carvacrol emulsion acidified with acetic acid on contaminated broccoli seeds [1,2]

| Treatment | Treatment Time (min) | Initial Inoculum (log CFU/g) | Cell Numbers after Treatment (log CFU/g) | Total Log Reduction | Pathogen Detected after Sprouting |
|---|---|---|---|---|---|
| Control | 30 | 8.0 ± 0.38 | 7.5 ± 0.05 | 0.45 ± 0.42 | + |
| | | 5.0 ± 0.19 | 4.4 ± 0.31 | 0.62 ± 0.38 | + |
| | | 3.2 ± 0.10 | 2.9 ± 0.64 | 0.61 ± 0.60 | + |
| | | 2.8 ± 0.53 | 2.1 ± 0.32 | 0.69 ± 0.88 | + |
| | 60 | 8.4 ± 0.43 | 7.9 ± 0.50 | 0.48 ± 0.92 | + |
| | | 4.9 ± 0.15 | 4.7 ± 0.69 | 0.53 ± 0.78 | + |
| | | 3.2 ± 0.23 | 2.8 ± 0.24 | 0.43 ± 0.42 | + |
| | | 2.6 ± 0.08 | 2.2 ± 0.24 | 0.45 ± 0.18 | + |
| 8000 ppm | 30 | 8.6 ± 0.30 | 5.3 ± 0.20 | 3.2 ± 0.38 | + |
| | | 5.7 ± 0.48 | 3.9 ± 0.73 | 1.9 ± 0.25 | + |
| | | 3.8 ± 0.22 | 2.7 ± 0.22 | 1.1 ± 0.08 | + |
| | | 2.6 ± 0.15 | ND | 2.6 ± 0.15 | − |
| | 60 | 8.7 ± 0.24 | 5.3 ± 0.36 | 3.4 ± 0.30 | + |
| | | 5.6 ± 0.73 | 4.0 ± 0.57 | 1.5 ± 0.82 | + |
| | | 3.9 ± 0.22 | 2.64 ± 0.04 | 1.3 ± 0.19 | + |
| | | 2.6 ± 0.23 | ND | 2.6 ± 0.23 | − |
| 4000 ppm | 30 | 8.4 ± 0.28 | 5.6 ± 0.14 | 2.8 ± 0.27 | + |
| | | 5.7 ± 0.41 | 4.6 ± 0.65 | 1.2 ± 0.45 | + |
| | | 3.8 ± 0.11 | 2.6 ± 0.30 | 1.3 ± 0.40 | + |
| | | 2.4 ± 0.08 | ND | 2.4 ± 0.08 | − |
| | 60 | 8.4 ± 0.66 | 5.2 ± 0.71 | 3.1 ± 0.78 | + |
| | | 5.7 ± 0.38 | 4.0 ± 0.36 | 1.7 ± 0.50 | + |
| | | 3.9 ± 0.48 | 2.5 ± 0.26 | 1.2 ± 0.33 | + |
| | | 2.6 ± 0.10 | ND | 2.6 ± 0.10 | − |

[1] All means and standard deviations are from triplicate studies. A "ND" indicates that no pathogens were detected using a three-tube MPN assay. Following treatment, seeds were germinated and tested for the presence of pathogens. A "+" indicates that pathogens were detected after germination. A "−" indicates that no pathogens were detected after germination.
[2] Total reduction averages within each treatment grouping were compared using Tukey's Test with a 95% confidence interval. Groupings of statistical significance are indicated by superscripted letters.

TABLE 5

Effect of carvacrol emulsion acidified with levulinic acid on sprout yield[1,2]

| Treatment | Treatment Time (min) | Mung Bean Yield | Broccoli Yield |
|---|---|---|---|
| Control | 30 | 78.3 ± 8.4[4] | 52.1 ± 5.6[4] |
|  | 60 | 75.2 ± 9.1[4] | 51.5 ± 11.7[4] |
| 8000 PPM | 30 | 77.4 ± 5.7[4] | 49.5 ± 3.1[4] |
|  | 60 | 78.6 ± 8.9[4] | 49.3 ± 1.9[4] |
| 4000 PPM | 30 | 84.4 ± 12.0[4] | 52.9 ± 11.0[4] |
|  | 60 | 92.1 ± 18.7[4] | 48.8 ± 3.5[4] |

[1]Bean yield averages were compared using Tukey's Test with a 95% confidence interval.
[2]All means and standard deviations are from triplicate studies.

TABLE 6

Effect of carvacrol emulsion acidified with acetic acid on sprout yield[1,2]

| Treatment | Treatment Time (min) | Mung Bean Yield | Broccoli Yield |
|---|---|---|---|
| Control | 30 | 78.3 ± 8.4[4] | 52.1 ± 5.6[4] |
|  | 60 | 75.2 ± 9.1[4] | 51.5 ± 11.7[4] |
| 8000 PPM | 30 | 81.6 ± 8.7[4] | 51.3 ± 2.5[4] |
|  | 60 | 79.1 ± 13.4[4] | 54.9 ± 10.2[4] |
| 4000 PPM | 30 | 84.4 ± 6.8[4] | 54.5 ± 11.7[4] |
|  | 60 | 83.8 ± 4.2[4] | 54.02 ± 5.5[4] |

[1]Bean yield averages were compared using Tukey's Test with a 95% confidence interval.
[2]All means and standard deviations are from triplicate studies.

Effectiveness of Acidified Carvacrol Nanoemulsion on *S. Enteritidis* Contaminated Baby Spinach Baby spinach was purchased from a local supermarket in Amherst, Mass. Spinach leaves were inoculated with five (5) 20 µL drops of a *Salmonella Enteritidis* cocktail for a final pathogen level of 8 to CFU/leaf. The inoculated leaves were then transferred to a sterile glass petri dish containing sterile filter paper (Fisher Scientific Cat #09-803-6D) within a biological safety cabinet and allowed to dry for 30 min at ambient temperatures. Semi-dried leaves where then stored overnight at 4° C. Inoculated leaves were then placed in sterile 50 mL conical tubes and treated by soaking in 30 mL of acetic acid acidified nanoemulsion (8000 ppm) for 2 min. Following treatment the leaf was dipped three times a 30 mL neutralizing buffer and then transferred to 30 mL of maximum recovery diluent (MRD) for 10 min. After soaking, the sample was vortexed for 20 secs and a dilution series was created and plated on the appropriate media and incubated at 37° C. for 24 hrs.

Effectiveness of an Acidified Carvacrol Nanoemulsion Against *Salmonella* spp. Contaminated Baby Spinach The effectiveness of an acetic acid acidified carvacrol nanoemulsion against *S Enteritidis* contaminated baby spinach can be seen in FIG. 4. A 2 min treatment with an acetic acid acidified 8000 ppm carvacrol nanoemulsion resulted in >4 log reduction of a *S. Enteritidis*. This data is very promising, and lends on to believe that this treatment system may be an acceptable, food-grade, GRAS antimicrobal treatment.

Figure 4:
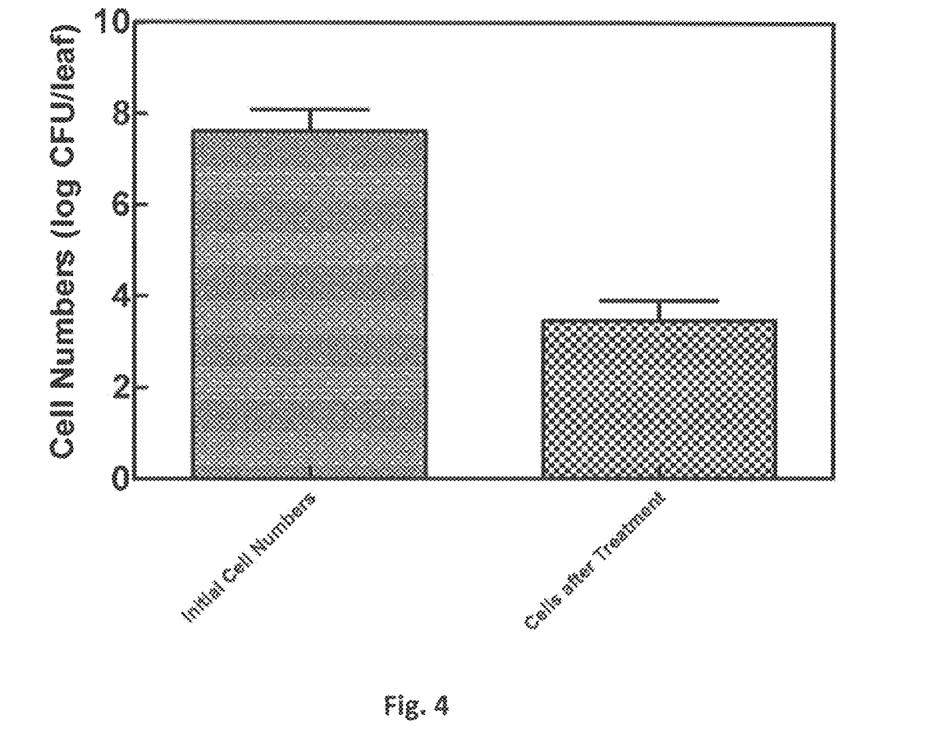
FIG. 4 shows the Number of surviving S. Enteritidis on baby spinach following a 2 min treatment with an acetic acid acidified 8000 ppm carvacrol nanoemulsion; Treatment resulted in >4 log reduction; All studies were performed in triplicate.

FIG. 4 shows the number of surviving *S. Enteritidis* on baby spinach following a 2 min treatment with an acetic acid acidified 8000 ppm carvacrol nanoemulsion. Treatment resulted in >4 log reduction. All studies were performed in triplicate.

Effectiveness of Acidified Carvacrol Nanoemulsion on *S. Enteritidis* Contaminated Stainless Steel Sterile stainless steel chips (5.1 cm×1.2 cm) were inoculated with a 100 µL drop of a *Salmonella Enteritidis* cocktail for final pathogen levels of 8 or 5 CFU/cm². Inoculated chips were then transferred to a sterile glass petri dish containing sterile filter paper (Fisher Scientific Cat #09-803-6D) within a biological safety cabinet and allowed to dry overnight at ambient temperatures. Inoculated chips were then placed in sterile 50 mL conical tubes and treated by soaking in 30 mL of acetic acid acidified nanoemulsion (8000 or 2000 ppm) for various time intervals. Following treatment, chips were dipped three times in 30 mL neutralizing buffer and then transferred to 30 mL of maximum recovery diluent (MRD) and allowed to soak for 10 min. After soaking, the sample was vortexed for 20 secs and a dilution series was created and plated on the appropriate media and incubated at 37° C. for 24 hrs.

For samples that would theoretically result in negative plate, a three tube most probable number (MPN) assay was used in conjunction with spread plating according to the FDA's Bacteriological Analytical Manual (BAM). Samples were appropriately diluted in Lactose Broth (BD BBL Cat #DF0004-17-7) *Salmonella* enrichment and incubated overnight. Dilution sets were checked for turbidity. Any positive tubes were streaked on XLD media (Remel Cat #R459902) for confirmation.

Effectiveness of an Acidified Carvacrol Nanoemulsion Against *Salmonella* spp. Contaminated Stainless Steel The effectiveness of an acetic acid acidified carvacrol nanoemulsion against *S. Enteritidis* stainless steel can be seen in Table 7. Treatment will 2000 ppm for all tested time points consistently produce ~5 log reduction of *S. Enteritidis*. Treatment of 5 log CFU/cm² of *S. Enteritidis* with 8000 ppm acidified emulsion for at least 5 mins reduced pathogen levels below our detection limit (≤3 MPN/Cm²). This data is very promising, and lends on to believe that this treatment system may be an acceptable, food-grade, GRAS antimicrobal treatment for household surfaces. Plus, the concentrations that would be used for this type of application are over 5-fold less than the stock emulsion which greatly increases the products shelf life. However, a full shelf life (>30 days) would have to be performed.

TABLE 7

The effect of an acidified carvacrol nanoemulsion against S. Enteridis contained stainless steel

| Treatment | Treatment time (min) | Initial inoculum (log CFU/cm²) | Cell numbers after treatment (log CFU/cm²) | Total log reduction |
|---|---|---|---|---|
| 2000 ppm | 2 | 6.91 ± 0.066 | 2.93 ± 0.980 | 4.66 ± 0.993 |
|  | 5 | 6.91 ± 0.066 | 1.90 ± 0.510 | 5.15 ± 0.572 |
|  | 10 | 7.14 ± 0.099 | 1.99 ± 0.107 | 5.14 ± 0.191 |
| 8000 ppm | 2 | 6.91 ± 0.066 | 2.33 ± 0.256 | 4.63 ± 0.320 |
|  |  | 5.30 ± 0.20 | 2.78 ± 0.98 | 2.98 ± 0.83 |
|  | 5 | 7.00 ± 0.045 | 2.69 ± 0.080 | 4.32 ± 0.081 |
|  |  | 5.33 ± 0.15 | ≤3 MPN |  |
|  | 10 | 7.00 ± 0.045 | 2.22 ± 0.664 | 5.04 ± 0.702 |
|  |  | 5.30 ± 0.20 | ≤3 MPN |  |

Fabrication of Acidified Eugenol Nanoemulsions by Spontaneous Emulsification and its Effectiveness Against *Salmonella* spp. Contaminated Mung Beans.

The preparation of the antimicrobial nanoemulsion was based on a method previously reported and cited above, but with a few modifications. Eugenol (4 g) was added to 6 g of medium chain triglyceride (MCT) oil (Miglyol 812, Witten, Germany) and thoroughly mixed with a magnetic stir bar for 5 min at 125 rpm. Once mixed, Tween 80® (10 g) (Sigma-Aldrich, P1754-500 ml) was added to the oil mixture and mixed with a magnetic stir bar for another 5 min at 125 rpm. The oil/Tween 80 mixture (20 g) was titrated, at a rate of 2 mL/min, into 80 g 50 mM levulinic (pH 2.8; Sigma-Aldrich, Cat #W262706) containing a magnetic stirring bar set to 600 rpm and allowed to mix for an additional 15 min. The emulsion was filter sterilized through a sterile 0.45 µm syringe filter (Fisher Scientific Cat #09-719-005) and stored in sterile 50 mL conical tubes at 2-5° C. for up to 3 weeks.

The effectiveness of the emulsion on mung beans was performed as previously described.

(1) Effectiveness of an Acidified Eugenol Nanoemulsion Against *Salmonella* spp. Contaminated Mung Bean.

Preliminary results show that a 30 min treatment with acidified (10 or 50 mM levulininc acid) 8000 ppm eugenol nanoemulsion consistently resulted in ~4 log reduction of *S. Enteritidis*. Contaminated mung beans (≤4 log CFU/g *S. Enteritidis*) treated with the acidified nanoemulsion for 30 min had remaining pathogen levels of ≤3 MPN/g, further demonstrating the effectiveness of acidified essential oil nanoemulsions.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue. The use of the word "about," avoids a strict numerical boundary to the specified parameter and its use can be understood in light of the technology embodied by the invention.

Although the teachings have been described with respect to various embodiments, it should be realized these teachings are also capable of a wide variety of further and other embodiments within the spirit and scope of the appended claims.

What is claimed is:

1. A method for producing an acidified, stable nanoemulsion having a desired droplet size and functional properties tailored for antimicrobial use as a food on surface disinfectant/sanitizer, the method comprising:
    blending an essential oil and a carrier oil to provide an oil mixture, and blending the oil mixture with a surfactant selected from Tween 20, Tween 40, Tween 60, Tween 80, Tween 85 and sodium dodecyl sulfate, thereby forming an organic phase;
    providing an aqueous phase comprising 50 mM of organic acid and having a pH of 2 to 4.5; and
    mixing the organic phase with the aqueous phase to provide the stable nanoemulsion wherein oil droplets are dispersed in the aqueous phase;
    wherein the stable nanoemulsion comprises between 2.5 weight % and 4 weight % of the essential oil, between 6 weight % and 7.5 weight % of the carrier oil, and between 5 weight % and 20 weight % of the surfactant, and wherein the aqueous phase completes 100% of the composition.

2. The method of claim 1 wherein the essential oil is selected from at least one of rosemary, rosemary, oregano, lemongrass, sage, clove, thyme, turmeric, tea bush oils, .alpha. terpineol, carvacrol, citral, eugenol, geraniol and thymol.

3. The method of claim 1 wherein the organic acid is selected from at least one of acetic acid, levulinic acid, citric acid, citrate, Lactic acid, Malic acid and Gluconic acid.

4. The method of claim 1 wherein the weight percentage of the surfactant is between 10 weight % and 20 weight %.

5. A method for treatment of pathogens in foods and surfaces, the method comprising: soaking an object to be treated, the object being one of the food or a surface, in a nanoemulsion produced by the method of claim 1.

6. The method of claim 5 wherein the essential oil is selected from at least one of rosemary, rosemary, oregano, lemongrass, sage, clove, thyme, turmeric, tea bush oils, .alpha. terpineol, carvacrol, citral, eugenol, geraniol and thymol.

7. The method of claim 5 wherein the organic acid is selected from at least one of acetic acid, levulinic acid, citric acid, citrate, Lactic acid, Malic acid and Gluconic acid.

8. The method of claim 5 wherein the weight percentage of the surfactant is between 10 weight % and 20 weight %.

* * * * *